US010330604B2

(12) United States Patent
Konishi et al.

(10) Patent No.: US 10,330,604 B2
(45) Date of Patent: Jun. 25, 2019

(54) AUTOMATED ANALYZER

(71) Applicant: Hitachi High-Technologies Corporation, Minato-ku, Tokyo (JP)

(72) Inventors: Rei Konishi, Tokyo (JP); Akihisa Makino, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/754,892

(22) PCT Filed: Jul. 25, 2016

(86) PCT No.: PCT/JP2016/071656
§ 371 (c)(1),
(2) Date: Feb. 23, 2018

(87) PCT Pub. No.: WO2017/033641
PCT Pub. Date: Mar. 2, 2017

(65) Prior Publication Data
US 2018/0259460 A1    Sep. 13, 2018

(30) Foreign Application Priority Data

Aug. 27, 2015  (JP) ................................ 2015-167355

(51) Int. Cl.
*G01N 21/82*  (2006.01)
*G01N 21/47*  (2006.01)
(Continued)

(52) U.S. Cl.
CPC ............. *G01N 21/82* (2013.01); *G01N 21/47* (2013.01); *G01N 21/77* (2013.01);
(Continued)

(58) Field of Classification Search
CPC .. G01N 21/82; G01N 21/47; G01N 35/00584; G01N 35/04; G01N 21/77; G01N 35/02
See application file for complete search history.

(56) References Cited

U.S. PATENT DOCUMENTS

2008/0063573 A1* 3/2008 Ammann .................. B01L 7/52
422/105
2008/0310999 A1* 12/2008 Yagi .................. G01N 35/00603
422/65
2014/0273245 A1   9/2014 Ochranek et al.

FOREIGN PATENT DOCUMENTS

EP    1 840 555 A1   10/2007
EP    2 381 243 A1   10/2011
(Continued)

OTHER PUBLICATIONS

International Search Report (PCT/ISA/210) issued in PCT Application No. PCT/JP2016/071656 dated Oct. 18, 2016 with English-language translation (Four (4) pages).
(Continued)

*Primary Examiner* — Benjamin R Whatley
(74) *Attorney, Agent, or Firm* — Crowell & Moring LLP

(57) ABSTRACT

An automated analyzer makes light from a light source incident on a liquid mixture consisting of a sample and a reagent in a reactor vessel and, by ascertaining with a photodetector the quantity of light transmitted or scattered and the change in the wavelength, performs quantitative and qualitative analysis of an object component. When light other than from the light source such as light from outside is incident on the photodetector, since it is no longer possible to accurately measure the quantity of light and the change in the wavelength, it is also no longer possible to accurately measure the analysis of the object component. In particular, in the constitution of an analysis unit provided with a plurality of analysis ports, during analysis at one analysis
(Continued)

port, due to various mechanisms accessing other analysis ports, disturbance light such as light reflected on this mechanism would enter the analysis port under analysis and sometimes have an effect on the measurement result. The present invention provides an automated analyzer that, by means of a first light shielding mechanism and a second light shielding mechanism having an opening part in an analysis unit provided with a plurality of analysis ports, does not allow disturbance light to be incident on the analysis port under analysis so that each mechanism is capable of accessing any analysis port.

11 Claims, 14 Drawing Sheets

(51) Int. Cl.
  *G01N 35/04* (2006.01)
  *G01N 35/00* (2006.01)
  *G01N 21/77* (2006.01)
  *G01N 35/02* (2006.01)

(52) U.S. Cl.
  CPC ....... *G01N 35/00584* (2013.01); *G01N 35/02* (2013.01); *G01N 35/04* (2013.01)

(56) References Cited

FOREIGN PATENT DOCUMENTS

| | | | |
|---|---|---|---|
| JP | 11-23580 A | | 1/1999 |
| JP | 2000-146825 A | | 5/2000 |
| JP | 2001-165937 A | | 6/2001 |
| JP | 2011-58901 A | | 3/2011 |
| JP | 2012-2733 A | | 1/2012 |
| JP | 2012002733 A | * | 1/2012 |
| JP | 2014-137319 A | | 7/2014 |

OTHER PUBLICATIONS

Japanese-language Written Opinion (PCT/ISA/237) issued in PCT Application No. PCT/JP2016/071656 dated Oct. 18, 2016 (three (3) pages).
Extended European Search Report issued in counterpart European Application No. 16838988.0 dated Mar. 28, 2019 (12 pages).

* cited by examiner

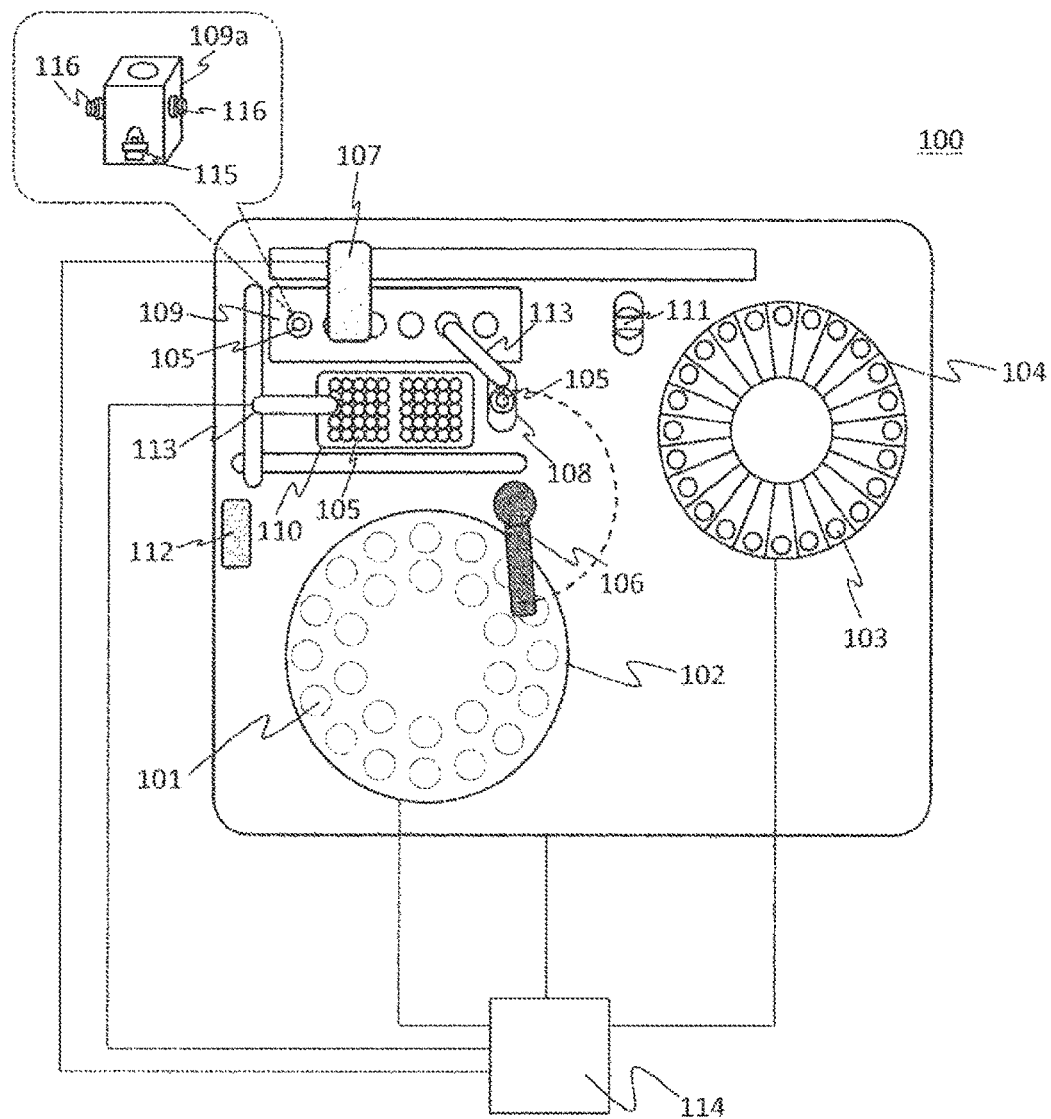
[Fig. 1]

[Fig. 2]
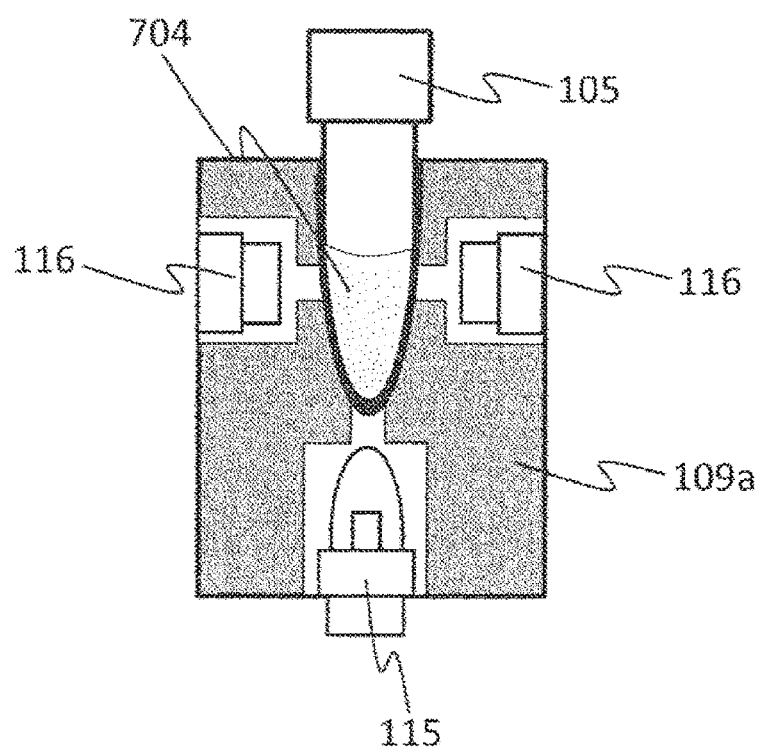

[Fig. 3]
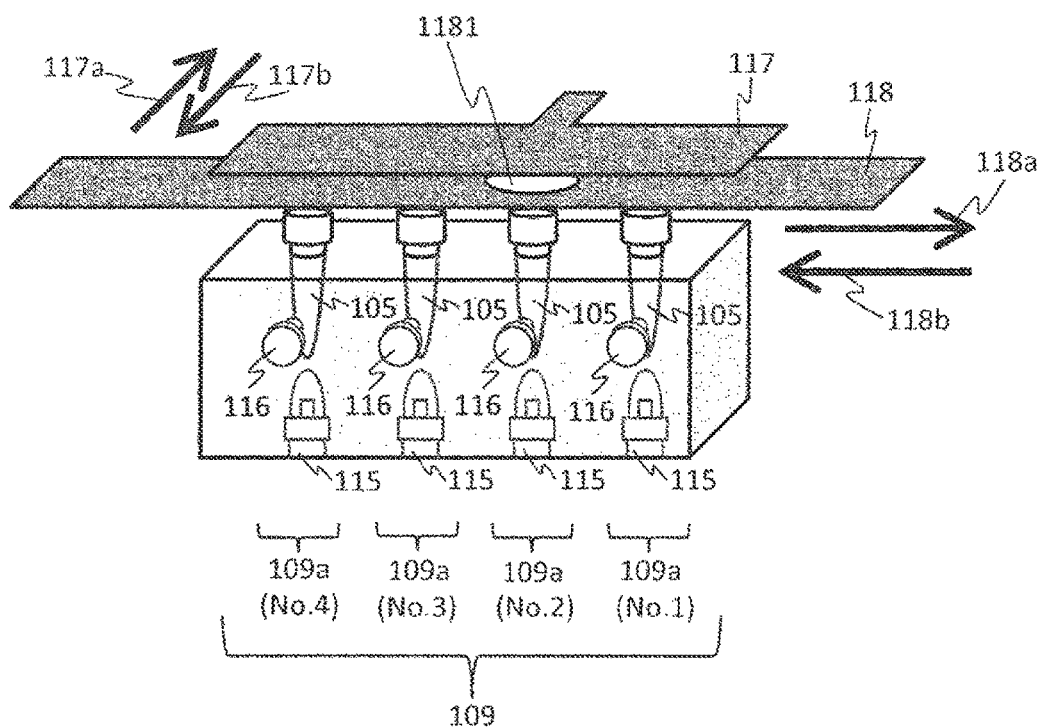

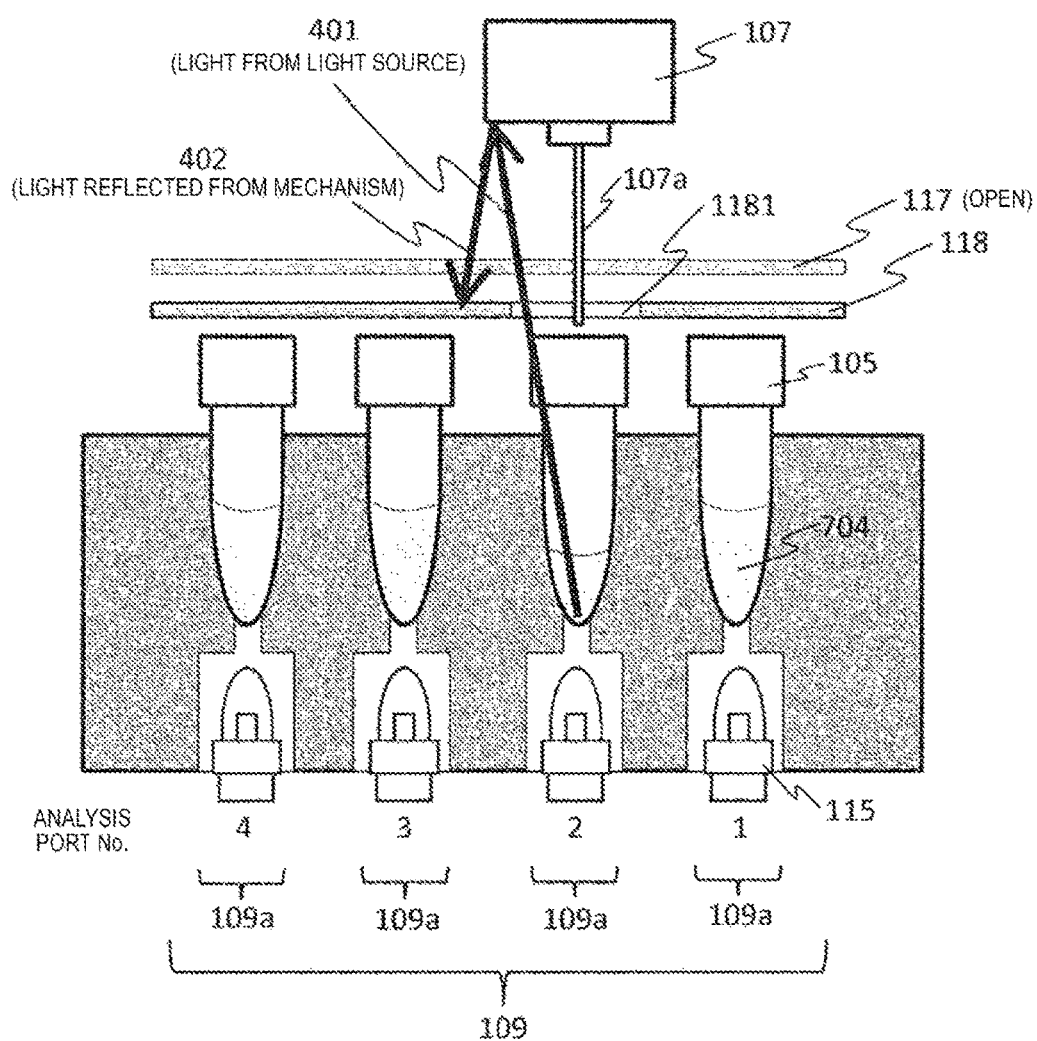
[Fig. 4]

[Fig. 5A]
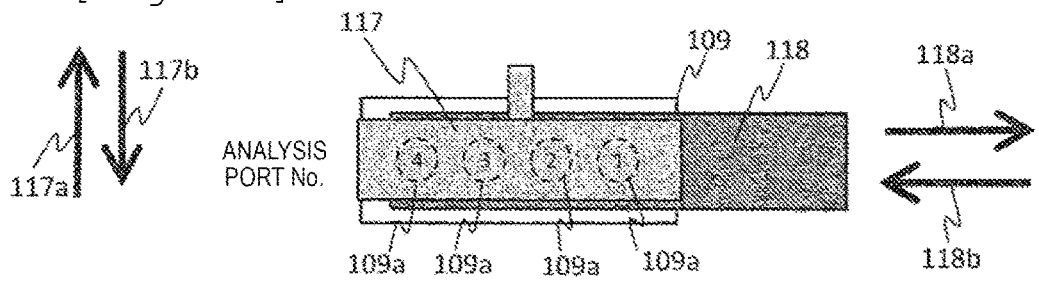
[Fig. 5B]
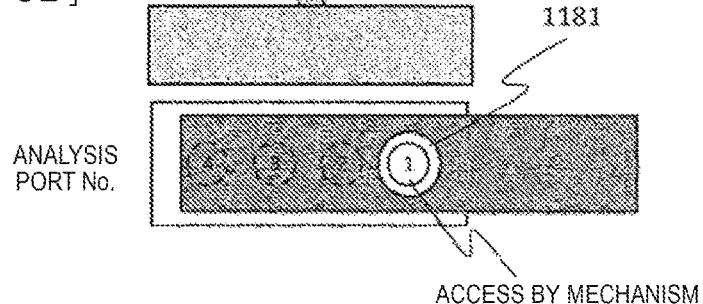
[Fig. 5C]
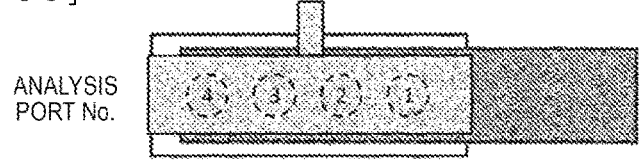
[Fig. 5D]
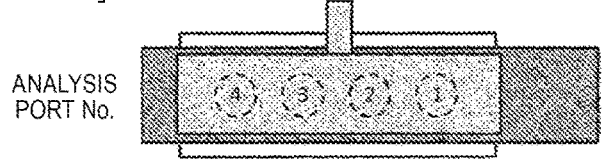
[Fig. 5E]
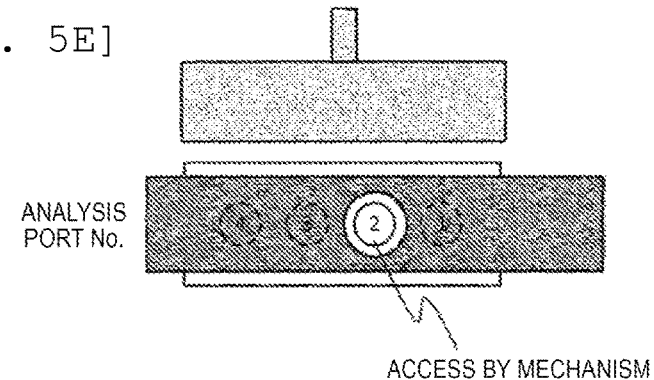

[Fig. 5F]
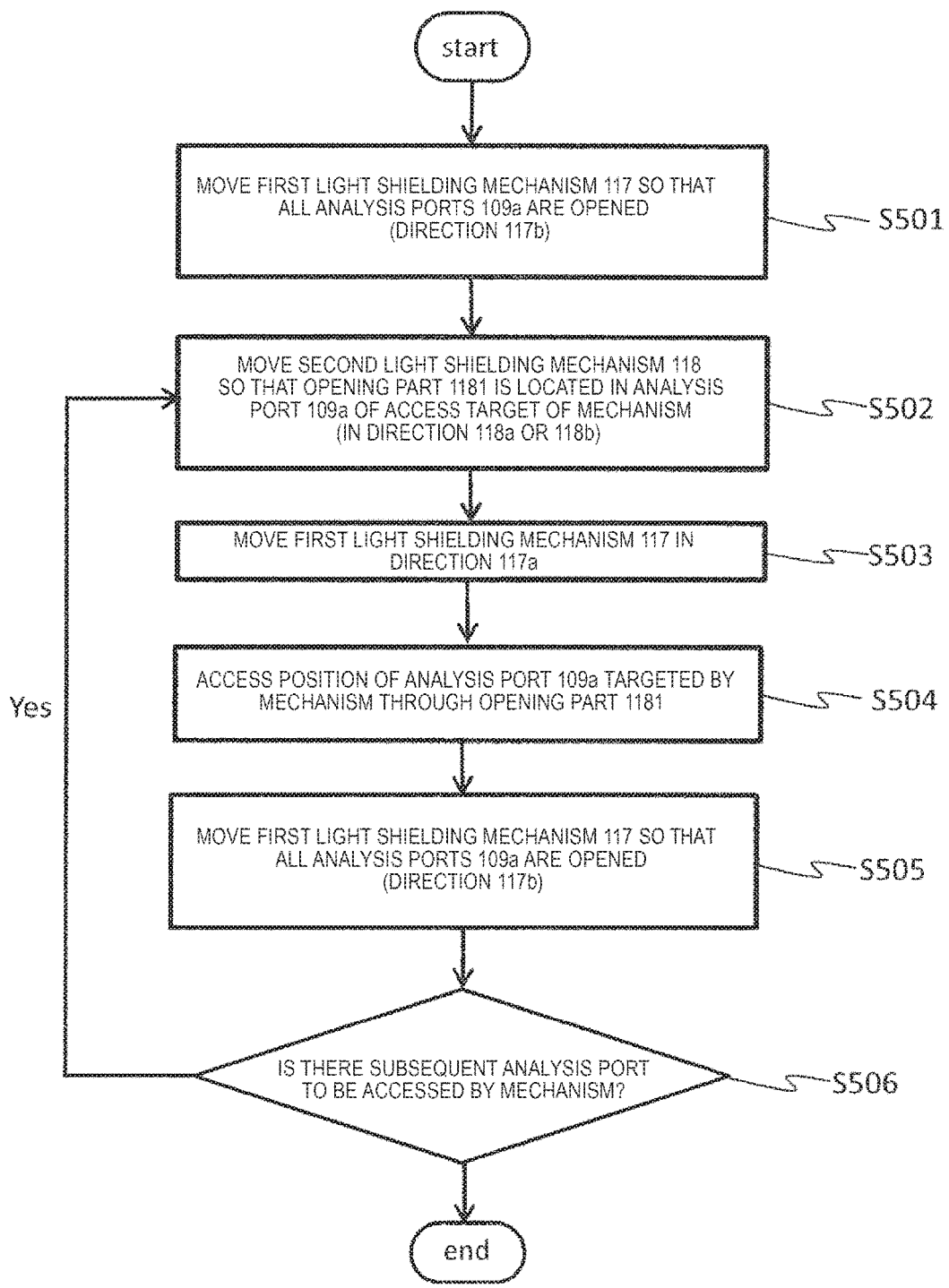

[Fig. 6]
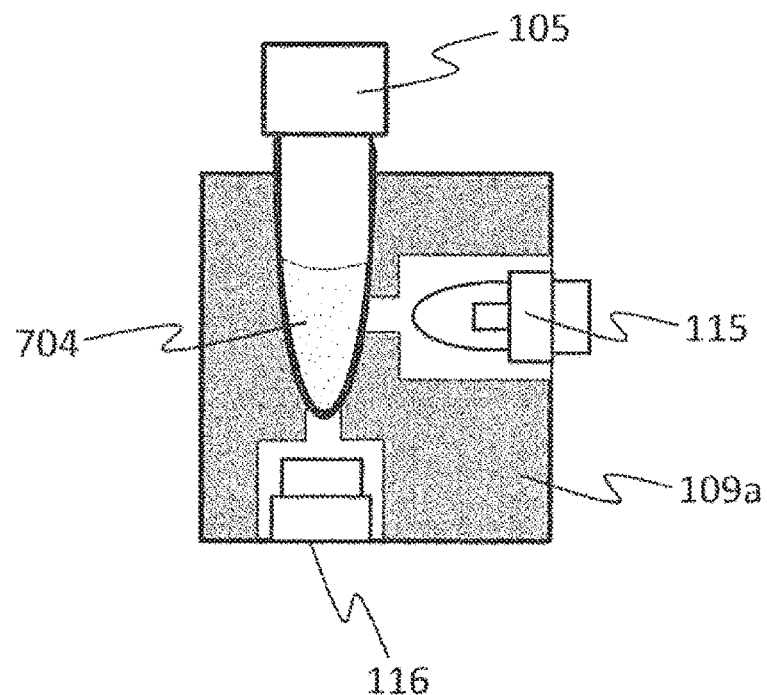
[Fig. 7]
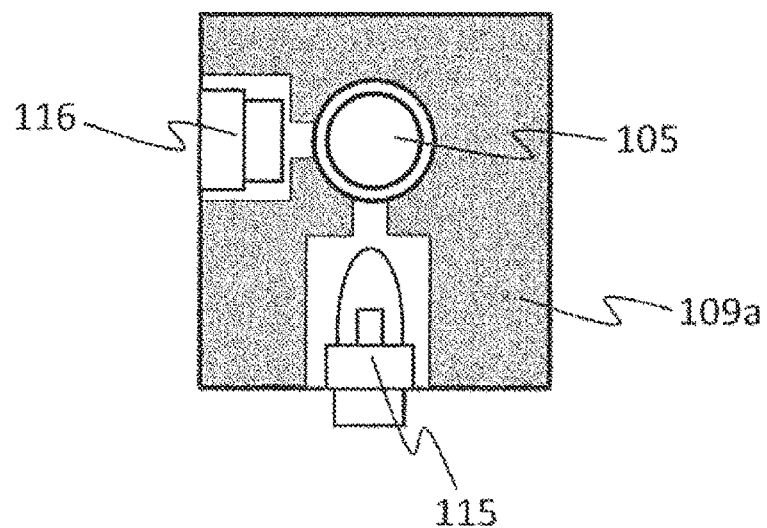

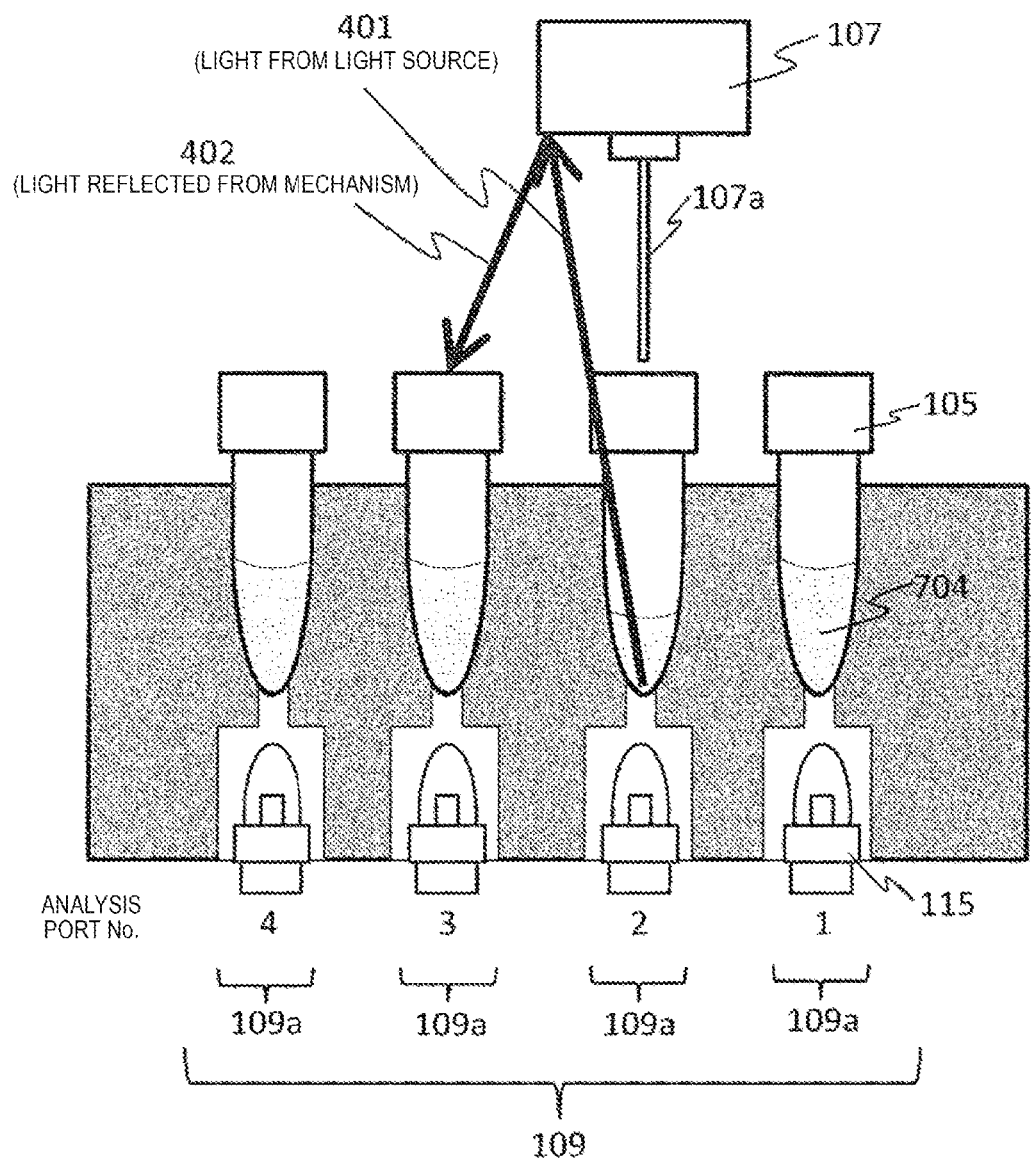
[Fig. 8]

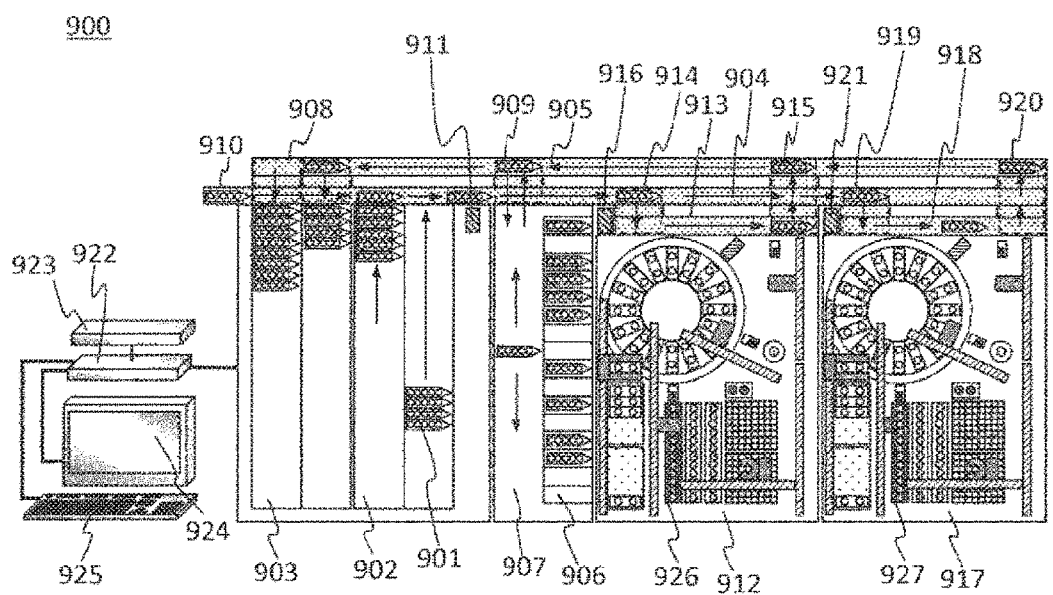
[Fig. 9]

[Fig. 10]
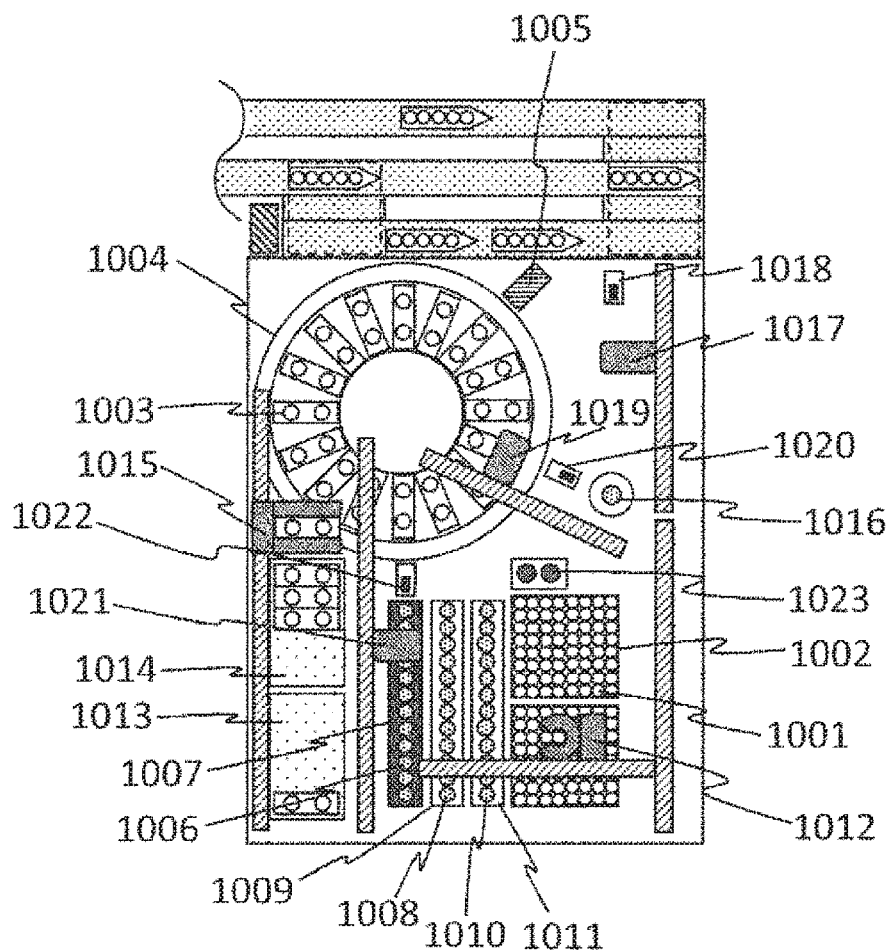

[Fig. 11]
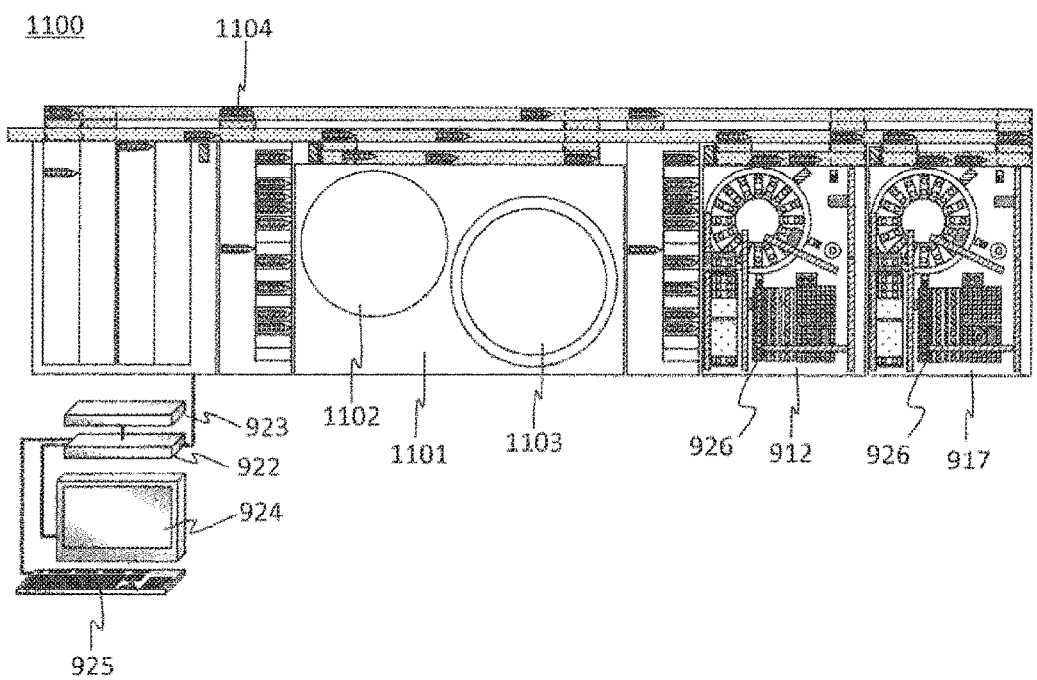

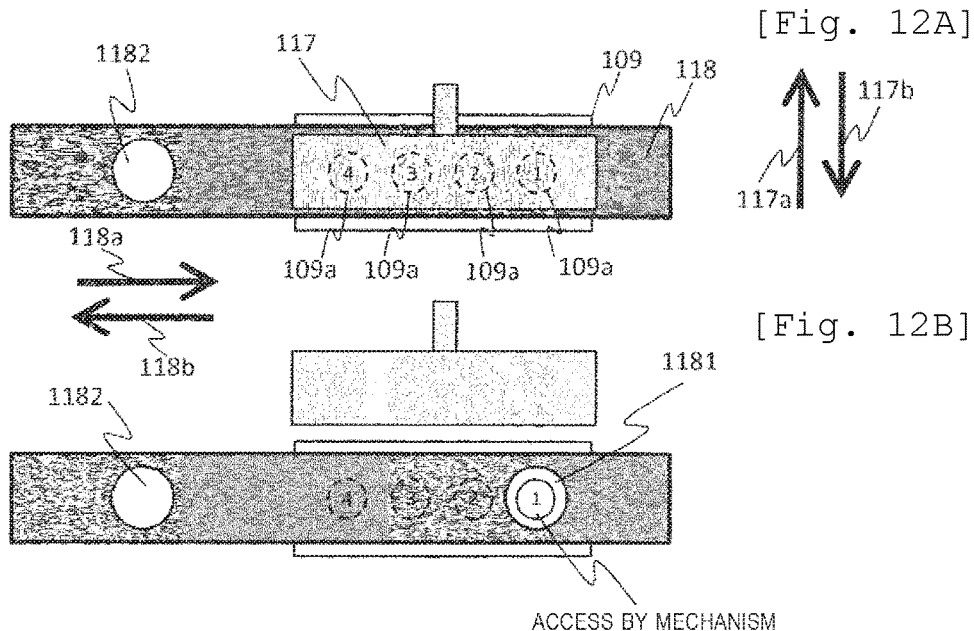
[Fig. 12A]
[Fig. 12B]
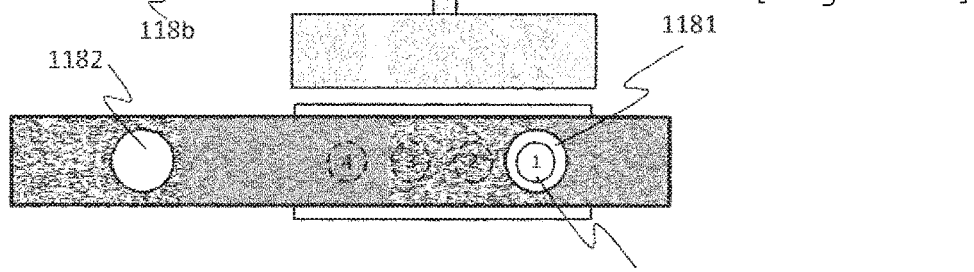
[Fig. 12C]
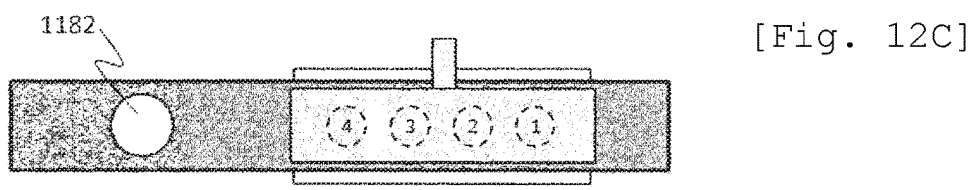
[Fig. 12D]
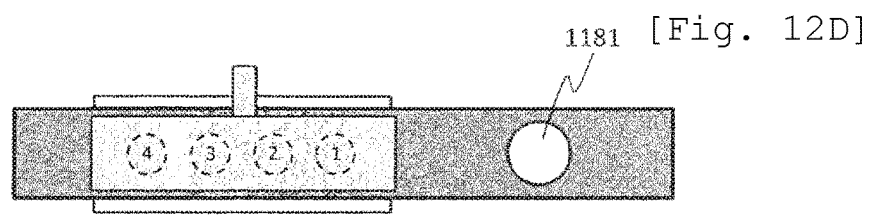
[Fig. 12E]
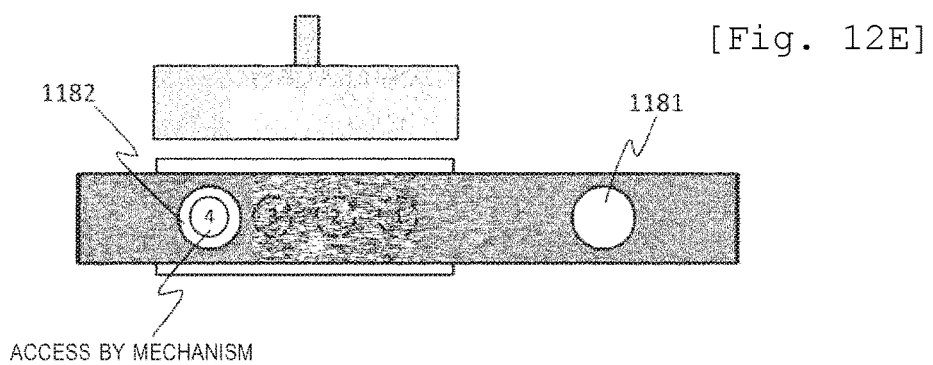

[Fig. 13A]
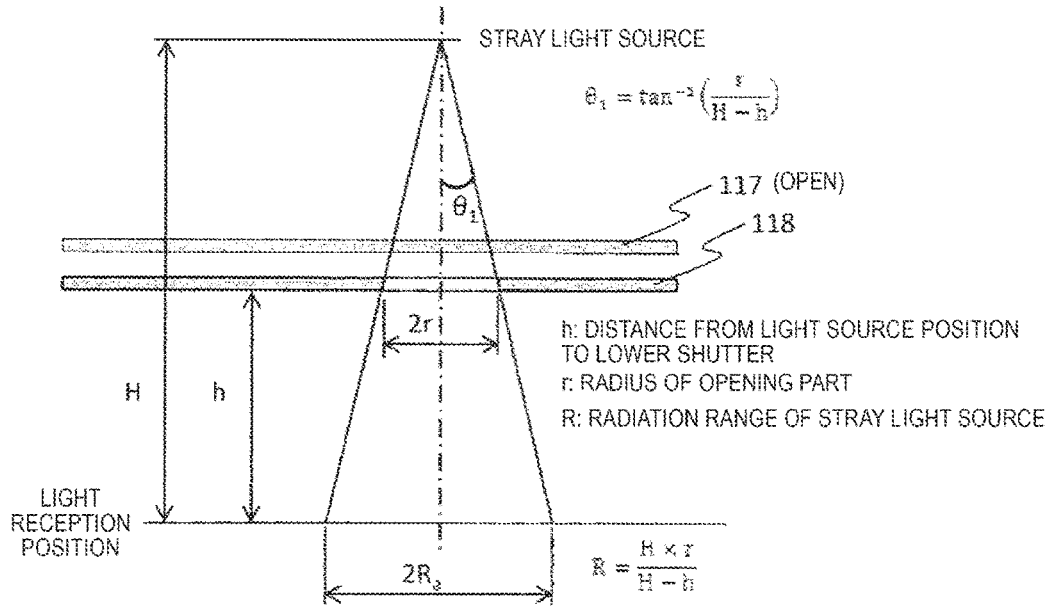
[Fig. 13B]
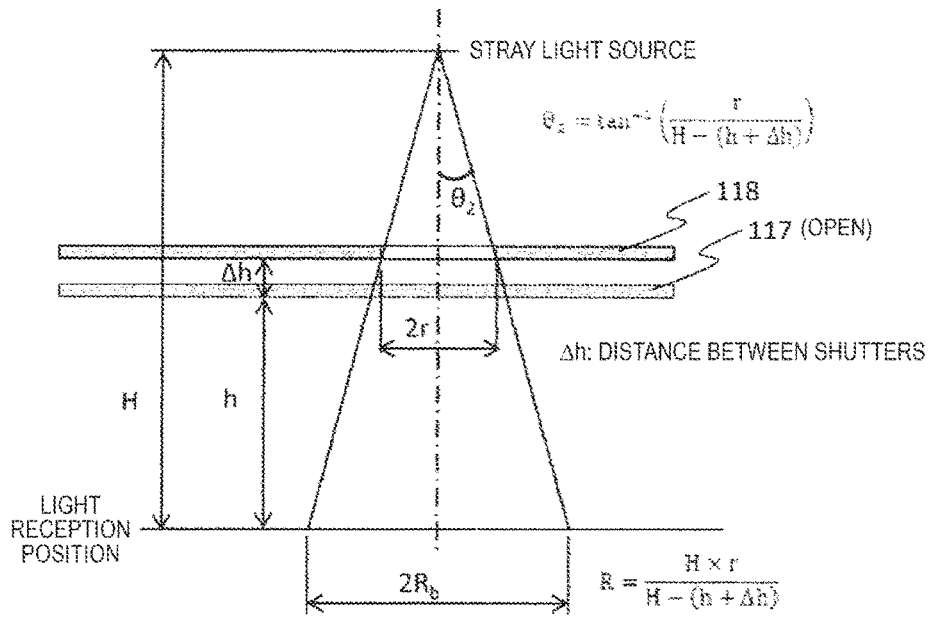

[Fig. 14]

| | | | | |
|---|---|---|---|---|
| REACTOR VESSEL TRANSFER MECHANISM | MOVE REACTOR VESSEL FROM MAGAZINE TO SAMPLE DISPENSATION PORT TO BE PROVIDED | DISCARD CERTAIN REACTOR VESSEL IN PORT No. n | MOVE REACTOR VESSEL AFTER SAMPLE DISPENSATION TO PORT No. n | MOVE TO HOME POSITION |
| ACCESS OF REACTOR VESSEL TRANSFER MECHANISM TO PORT No. n | | GRASP REACTOR VESSEL AFTER ANALYSIS | PROVIDE REACTOR VESSEL | |
| REAGENT DISPENSATION MECHANISM | MOVE TO CLEANING TANK TO CLEAN NOZZLE | | MOVE ONTO REAGENT PORT AND SUCK REAGENT | MOVE ONTO PORT No. n |
| ACCESS OF REAGENT DISPENSATION MECHANISM TO PORT No. n | | | | EJECT REACTOR VESSEL ON PORT No. n |
| SAMPLE DISPENSATION MECHANISM | SUCK SAMPLE FROM SAMPLE VESSEL | EJECT SAMPLE TO REACTOR VESSEL | | |
| FIRST LIGHT SHIELDING MECHANISM | CLOSED | OPEN | CLOSED | OPEN |
| SECOND LIGHT SHIELDING MECHANISM | MOVE ONTO PORT No. n | | | | n = 1, 2, 3, ...

AUTOMATED ANALYZER

TECHNICAL FIELD

The present invention relates to an automated analyzer automatically analyzing a component contained in a biological sample such as blood and, in particular, to a technology for an automated analyzer including a plurality of analysis ports that include a light source radiating light to an analysis target and a detector detecting the light radiated from the light source.

BACKGROUND ART

As devices analyzing object components contained in biological samples such as blood, automated analyzers that measure a quantity of light of transmitted light or scattered light with a single wavelength or a plurality of wavelengths obtained by radiating light from light sources to a reaction liquid which is an analyzer and in which a sample and a reagent are mixed are widely used.

As automated analyzers, there are devices for biochemical analysis performing quantitative and qualitative analysis of object components in biological samples and devices for blood coagulation analysis measuring coagulability of blood which is a sample, for example, in fields of biochemical examination or hematologic examination.

In either analysis, quantitative or qualitative analysis of an object component is performed by ascertaining the quantity of light from a light source or a change in the wavelength with a photodetector. When light other than light from a light source, such as light from outside is incident on the photodetector, since it is no longer possible to accurately measure the quantity of light and the change in the wavelength, it is also no longer possible to accurately measure the analysis of the object component.

In regard to a technology for preventing light from outside from entering the photodetector, PTL 1 discloses a technology for protecting a light-receiving element from excessive light when two light shielding mechanisms having opening parts are provided and a measurement vessel is mounted on a detector.

PTL 2 discloses a constitution including: a light shielding member that is provided below a test tube installation position, shields light incident on a detector in a state other than photometry, that is, in a state in which a test tube is not provided in a measurement chamber, moves down while pushing the test tube when the test tube is inserted into the measurement chamber, and enables light from a measurement target to be incident on the detector; and a cover that is provided above the test tube at the time of measurement and covers an opening part.

PLT 3 discloses a technology for providing a shutter mechanism that shields a gap between a measurement part on a cuvette mounting position of the measurement part and a reagent dispensation mechanism and hiding the cuvette mounting position by the shutter mechanism when the reagent dispensation mechanism reciprocates on the measurement part.

CITATION LIST

Patent Literature

PTL 1: JP-A-2012-002733
PTL 2: JP-A-2000-146825
PTL 3: JP-A-2001-165937

SUMMARY OF INVENTION

Technical Problem

In recent years, to meet a request for increasing the number of analysis processes or increasing the number of analysis items, importance of an automated analyzer including a plurality of analysis ports further increases. To efficiently advance an analysis process in a constitution in which a plurality of analysis ports are included, it is preferable to simultaneously perform photometry of a sample and access to analysis ports of various mechanisms such as sample or reagent dispensation mechanisms.

However, in the constitution of the light shielding mechanisms disclosed in PTL 1, since it is necessary to shield the photodetector from light when various mechanisms access an analysis unit, photometry of a sample may not be performed during the access. That is, the above-described two operations may not simultaneously be performed.

In the constitution of the light shielding mechanism disclosed in PTL 2, as described above, the light shielding member including a spring can shield the photodetector from light to protect the photodetector at the time of inserting or discharging a test tube. However, the light shielding member originally does not function in a case in which a test tube is provided in a measurement chamber. For the cover member shielding the opening part of the test tube from light at the time of photometry in this patent document, it is necessary to individually prepare the cover members by the number of analysis ports in a case of application to the plurality of analysis ports. In this case, the photometry of a sample and access to the analysis ports can be simultaneously performed, but there is a problem in terms of cost or a device space.

For the constitution of the light shielding mechanism disclosed in PTL 3, in a case in which a single light shielding mechanism common to the plurality of analysis ports is provided, it is necessary to open the analysis ports in order for various mechanism to access other analysis ports, for example, during photometry of a sample at a certain specific analysis port. At this time, there is a possibility that light from a light source in the analysis port during photometry affects a photometry result because light reflected toward another structure such as a dispensation mechanism or light entering from outside is detected by a detector.

An object of the present invention is to perform analysis at a high speed by efficiently performing an operation on each analysis port even in a constitution in which a plurality of analysis ports are included and to realize high-reliable analysis while suppressing an influence of noise on a measurement result.

Solution to Problem

According to an aspect of the present invention for solving the foregoing problem, an automated analyzer includes: a reactor vessel that accommodates a liquid mixture consisting of a sample and a reagent; a dispensation mechanism that dispenses the sample and the reagent to the reactor vessel; an analysis unit that includes a plurality of analysis ports each including an optical system formed by a light source radiating light to the reactor vessel accommodating the liquid mixture and a photodetector unit receiving the light radiated from the light source; a first light shielding mechanism that shields all the analysis ports from light among the plurality of analysis ports; a second light shielding mechanism that includes an opening part and shields some of the analysis ports from light among the plurality of analysis ports; and a control unit that controls operations of the dispensation mechanism, the first light shielding mechanism, and the second light shielding mechanism. The control unit moves the second light shielding mechanism to place the opening part at a position of a predetermined analysis port in a state in which all the analysis ports are shielded from light by the first light shielding mechanism. The first light shielding mechanism is moved so that the light shielding by the first light shielding mechanism is excluded after the second light shielding mechanism is moved.

Advantageous Effects of Invention

According to the aspect of the present invention, in the automated analyzer including the plurality of analysis ports, the analysis port performing photometry of the sample is reliably shielded from light and the other arbitrary analysis ports are opened meanwhile so that the dispensation mechanism or the like accesses the analysis ports. Therefore, an influence of noise on a measurement result is reduced, which contributes to realization of high precise and high speed analysis.

BRIEF DESCRIPTION OF DRAWINGS

FIG. 1 is a diagram illustrating a basic constitution of an automated analyzer according to an embodiment.

FIG. 2 is a sectional view illustrating the constitution of an analysis port according to an embodiment (a first embodiment).

FIG. 3 is a perspective view illustrating a basic constitution of an analysis unit including light shielding mechanisms according to the embodiment (the first embodiment).

FIG. 4 is a sectional view illustrating the constitution of the light shielding mechanisms at the time of sample dispensation in the analysis unit according to the embodiment (the first embodiment).

FIGS. 5A to 5E are top views illustrating an operation of the light shielding mechanisms at the time of sample dispensation in the analysis unit according to the embodiment (the first embodiment).

FIG. 5F is a flowchart illustrating the operation of the light shielding mechanisms at the time of sample dispensation in the analysis unit according to the embodiment (the first embodiment).

FIG. 6 is a sectional view illustrating the constitution of the analysis port according to an embodiment (a third embodiment).

FIG. 7 is a sectional view illustrating the constitution of the analysis port according to an embodiment (a fourth embodiment).

FIG. 8 is a sectional view illustrating the constitution of an analysis unit of the related art including a plurality of analysis ports.

FIG. 9 is a diagram illustrating a basic constitution of an automated analyzer including blood coagulation analysis units of two modules according to an embodiment (a fifth embodiment).

FIG. 10 is a diagram illustrating the constitution of the blood coagulation analysis unit in the automated analyzer according to the embodiment (the fifth embodiment).

FIG. 11 is a diagram illustrating a basic constitution of an automated analyzer including a biochemical analysis unit and a blood coagulation analysis unit according to an embodiment (a sixth embodiment).

FIGS. 12A to 12E are top views illustrating an operation of a light shielding mechanism at the time of sample dispensation in an analysis unit according to an embodiment (a second embodiment).

FIGS. 13A and 13B are diagrams illustrating a relation between disposition of first and second light shielding mechanisms and a light shielding range according to the embodiment (the first embodiment).

FIG. 14 is a time chart illustrating an operation at the time of an analysis operation in the analysis unit according to the embodiment (the first embodiment).

Hereinafter, modes for carrying output the present invention will be described in detail with reference to the drawings. The same reference numerals are given to constituent elements having the same functions as a whole, and the description thereof will be omitted.

FIRST EMBODIMENT

<Overall Configuration of Device>

FIG. 1 is a diagram illustrating a basic constitution of an automated analyzer according to an embodiment. Here, an example of a device performing blood coagulation analysis will be described as a type of an automated analyzer. As illustrating the drawing, an automated analyzer 100 mainly includes a sample disk 102, a reagent disk 104, a sample dispensation mechanism 106, a reagent dispensation mechanism 107, a sample dispensation port 108, an analysis port 109, a reactor vessel supply unit 110, a first light shielding mechanism 117, a second light shielding mechanism 118, a reactor vessel transfer mechanism 113, and a control unit 114.

The sample disk 102 is a unit with a disk shape rotatable clockwise and counterclockwise and a plurality of sample vessels (reagent vessels) 101 accommodating a sample such as a standard sample or an examined sample can be disposed on the circumference of the sample disk 102.

The reagent disk 104 is a unit with s disk shape rotatable clockwise and counterclockwise and a plurality of reagent vessels 103 accommodating reagents containing components that react with examination items included in the samples can be disposed on the circumference of the reagent disk 104, as in the sample disk 102. Although not illustrated in the drawing, the reagent disk 104 can also be configured such that the reagents in the disposed reagent vessels 103 can be coldly reserved by providing a cold reserving mechanism.

The reactor vessel transfer mechanism 113 transports a reactor vessel 105 used for analysis to carry in from the reactor vessel supply unit 110 to the sample dispensation port 108. After dispensation of the sample, the reactor vessels 105 are carried out from the sample dispensation port 108 and are transported to be carried in the analysis port 109. After the analysis ends, the reactor vessel 105 in the analysis port 109 is carried out to be transported to the reactor vessel discarding unit 112.

The sample dispensation mechanism 106 sucks the sample in the sample vessels 101 held in the sample disk 102 and dispenses the sample into the reactor vessels 105 provided in the sample dispensation port 108. Here, an operation of the sample dispensation mechanism 106 is controlled based on an instruction of the control unit 114 in association with an operation of a sample syringe pump (not illustrated).

The reagent dispensation mechanism 107 sucks the reagent in the reagent vessels 103 held in the reagent disk 104 and dispenses the reagent into the reactor vessels 105 which is provided in the analysis port 109 and to which the sample is dispensed. Here, an operation of the reagent dispensation mechanism 107 is controlled based on an instruction of the control unit 114 in association with an operation of a reagent syringe pump (not illustrated).

A cleaning mechanism 111 cleans the sample dispensation mechanism 106 and the reagent dispensation mechanism 107.

As a whole, the control unit 114 performs control such as operations and condition settings of various constitutions of the automated analyzer 100, such as opening and closing operations of the sample disk 102, the reagent disk 104, the first light shielding mechanism 117, the second light shielding mechanism 118, horizontal and vertical operations of the sample dispensation mechanism 106 and the reagent dispensation mechanism 107, operations of the sample syringe pump and the reagent syringe pump (not illustrated), a supply operation for cleaning water (not illustrated) in the cleaning mechanism 111, operations of a light source 115 and photodetector units 116 of an analysis port 109a, and a data processing operation such as calculation of a blood coagulation time based on a detection result or a density of an object component. The control unit 114 in the drawing is connected to each constituent element and controls the whole automated analyzer, but can also be configured to include a control unit independent for each constituent unit.

<Constitution of Analysis Port>

FIG. 2 is a sectional view illustrating a basic constitution of each analysis port in the analysis unit in the automated analyzer according to the embodiment. In the analysis port 109, a groove is formed to install the reactor vessel 105. As illustrated in FIG. 1, the plurality of analysis ports 109a are provided in the analysis unit 109 of the automated analyzer according to the embodiment.

Accordingly, the reactor vessel 105 is provided in each analysis port 109a, and thus a plurality of samples can be simultaneously analyzed. In FIG. 1, the constitution in which the plurality of analysis ports 109a are disposed in a line in the analysis unit 109 has been described, but the present invention is not limited thereto, but can be applied to various constitutions in accordance with constitutions or operations of the other mechanisms. For example, in a case in which the reagent dispensation mechanism 107 or the reactor vessel transfer mechanism 113 is configured to perform rotary movement rather than the above-described horizontal movement, the present invention can be applied to various configurations of the analysis unit 109 in accordance with configurations or operations of another mechanism. For example, the plurality of analysis ports 109a can be provided along the circumference of the analysis unit 109 with a circular disk shape.

Each analysis port 109a includes the light source 115 and the photodetector units (detectors) 116 in one accommodated reactor vessel 105. FIG. 2 illustrates the constitution in which one light source 115 and two photodetector units 116 are provided for one reactor vessel 105, but the present invention is not limited thereto. For example, according to analysis conditions or the like, the number of photodetector units 116 can be set to one or can also be set to three or more for one reactor vessel 105. The present invention can be applied to various constitutions as necessary. For example, the number of light sources 115 can be similarly set to 2 or more or one light source 115 can be set to 1 for the plurality of reactor vessels 105.

As illustrated in the drawing, the light source 115 is installed below the reactor vessel 105 held in the analysis port 109a and the photodetector units 116 are installed on side surfaces of the reactor vessel 105 held in the analysis port 109a and is at a height below the height of a liquid surface in a state in which a whole quantity of reaction liquid 704 (referring to a liquid mixture consisting of a sample and a reagent) is accommodated. The light from the light source 115 is radiated from the lower side to the reaction liquid 704 in the reactor vessel 105 provided in the analysis port 109a, and thus is scattered by deposits produced by reaction occurring in the reaction liquid. As the deposits increases, the scattered light also increases. Therefore, when the photodetector units (detectors) 116 detect the scattered light, a quantity of deposits can be obtained.

For example, when the sample and the reagent react with each other in a blood coagulation examination item, fibrin is deposited over time. Then, the quantity of light scattered with the deposition of the fibrin is also increased. By detecting the quantity of light, it is possible to obtain a quantity of fibrinogen (Fbg) in the sample. By similarly monitoring the amount of light using a reagent corresponding to each examination item, it is also analyze other blood coagulation examination items such as a prothrombin time (PT) and an activated partial thromboplastin time (APTT). For example, as illustrated in the drawing, in a case in which the light source 115 is disposed below the reactor vessel 105 provided in the analysis port 109a and the two photodetector units (detectors) 116 are disposed to face each other at 90° with respect to an optical axis of the light source 115, the light radiated from the light source 115 below the accommodated reactor vessel 105 is scattered due to the deposits of fibrin in the reaction liquid, and the amount of scattered light increases with an increase in the deposit of the fibrinogen and is detected by the photodetector units (detectors) 116.

<Analysis Unit>

FIG. 3 is a perspective view illustrating a basic constitution of the analysis unit including the light shielding mechanisms according to the embodiment. As described above, the analysis unit 109 according to the embodiment is configured to include the plurality of analysis ports 109a. Here, the analysis unit 109 includes a first light shielding mechanism 117 and a second light shielding mechanism 118 above the accommodated reactor vessels 105.

The first light shielding mechanism 117 includes a driving unit (not illustrated in the drawing) that performs opening and closing and moves in directions 117a and 117b in the drawing to perform opening and closing operations based on an instruction of the control unit 114 illustrated in FIG. 1. That is, when the first light shielding mechanism 117 is moved in the direction 117a on the rear side of the sheet surface to open each analysis port 109a of the analysis unit 109. The first light shielding mechanism 117 is moved in the direction 117b on the front side of the sheet surface to shield each analysis port 109a of the analysis unit 109 from light.

The second light shielding mechanism 118 is provided between the first light shielding mechanism 117 and the analysis unit 109. In the second light shielding mechanism 118, an opening part 1181 is formed so that a mechanism such as a dispensation mechanism can access the analysis port 109a at any position. Here, the size of the opening part 1181 is set to a size by which there is no interference at the time of accessing the mechanism such as the sample dispensation mechanism 106, the reagent dispensation mechanism 107, or the reactor vessel transfer mechanism 113 and the reactor vessel 105 accommodated in the analysis port 109a at an adjacent position is hidden when viewed from the upper side. For example, when the diameter of the reactor vessel is about 7 mm, an interval of the analysis ports 109a is about 18 mm, the diameter of the opening part 1181 may be equal to or greater than 7 mm and equal to or less than 29 mm. Here, as the diameter of the opening part is smaller, an influence of disturbance light can decrease. Therefore, the diameter of the opening part is preferably set to a minimum diameter necessary when the mechanism accesses the analysis port 109a.

The second light shielding mechanism 118 includes a driving unit (not illustrated in the drawing) that moves the position of the opening part and operates in directions oriented along a direction in which the reactor vessels 105 of the plurality of analysis ports 109a are arrayed, that is, the directions 118a and 118b, based on an instruction of the control unit 114. That is, in the example of the constitution illustrated in the drawing, when the second light shielding mechanism 118 is moved in the right direction 118a in the drawing, the opening part 1181 is moved from a position of No. 2 to a position of No. 1 of the analysis port 109a. When the second light shielding mechanism 118 is moved in the left direction 118b in the drawing, the opening part 1181 is moved from the position of No. 2 to a position of No. 3 or No. 4 of the analysis port 109a. In the drawing, the constitution in which the opening part 1181 of the second light shielding mechanism 118 is provided at one position is illustrated, but the present invention is not limited thereto, but can be applied to various constitutions. For example, the opening parts can be set at two positions according to the analysis conditions.

A constitution in which the second light shielding mechanism 118 includes the opening parts 1181 at two positions will be described in a second embodiment.

<Operation of Light Shielding Mechanism>

FIG. 4 is a sectional view illustrating the constitution of the light shielding mechanisms at the time of sample dispensation in the analysis unit according to the embodiment. In the drawing, the reagent dispensation mechanism 107 is starting to perform a reagent ejecting operation on the reactor vessel 105 disposed at the position of No. 2 of the analysis port 109a. As illustrated in the drawing, when the reagent dispensation mechanism 107 is ejecting the reagent to the reactor vessel 105 disposed at the position of No. 2 of the analysis port 109a, it is necessary for the first light shielding mechanism to be moved in the direction on the rear side of the sheet surface with respect to the analysis unit 109 to open each analysis port 109a of the analysis unit 109.

Here, FIG. 8 is a sectional view illustrating the constitution of an analysis unit of the related art including a plurality of analysis ports. That is, all the analysis ports 109a in the analysis unit 109 are open without including the first light shielding mechanism 117 and the second light shielding mechanism 118 according to the embodiment.

When light is incident on the analysis ports 109a during analysis of disturbance light in a case in which a liquid mixture consisting of a sample and a reagent has turbidity, the incident light is scattered and incident on the photodetector unit (detector) 116, and thus the light causes irregularity of photometry data. For example, as one of the disturbance light, light from the light source 115 of the analysis port 109a is used for description. As illustrated in the drawing, light 401 incident on the reactor vessel 105 in which the reaction liquid 704 is accommodated from the light source 115 of the analysis port 109a hits the reagent dispensation mechanism 107 during the photometry operation, which is located above the reactor vessel 105, to be reflected. As a result, reflected light 402 occurring due to the hitting is incident in a direction of No. 3 of the adjacent analysis port 109a which is performing a photometry operation and is detected by the photodetector units (detectors) 116 (not illustrated) in the analysis port 109a at this position, and thus the reflected light 402 becomes noise. Here, even when a light shielding mechanism (equivalent to the first light shielding mechanism 117 according to the embodiment) that serves to shield all the analysis ports 109a from light or open all the analysis ports 109a of the analysis unit 109, all the analysis ports 109a have to be opened in this constitution in order to allow the reagent dispensation mechanism 107 to access one analysis port 109a. Therefore, reflected light 402 occurring due to the hitting with the reagent dispensation mechanism 107 enters in the direction of the position of the analysis port 109a during the photometry operation and causes noise. Further, at this time, in order to suppress an influence of the noise, it can also be considered to turn off the light source of the analysis port 109a which is an access target of the mechanism. However, since a change in the quantity of light immediately after turning on the light source increases due to a change in heat or a current. Therefore, this consideration is not suitable for a case of an analysis condition that measurement starts immediately after a reagent is ejected to a sample particularly as in a blood coagulation analyzer.

Here, referring back to FIG. 4, in the analysis unit 109 including the light shielding mechanisms according to the embodiment in contrast to the above-described constitution of the related art, the second light shielding mechanism 118 serves to block the reflected light 402 occurring due to the hitting with the reagent dispensation mechanism 107. Therefore, there is no influence on the photometry operation of No. 3 of the adjacent analysis port 109a. Even when a traveling direction of the reflected light 402 is different from the direction illustrated in the drawing, it is possible to prevent the reflected light from entering any position except for No. 2 of the analysis port 109a.

Then, at the position of No. 2 of the analysis port 109a, the reagent dispensation mechanism 107 accesses the reactor vessel 105 through the opening part 1181 of the second light shielding mechanism 118 to eject the reagent.

In the above-described constitution, for example, the case in which the reagent dispensation mechanism 107 accesses the reactor vessel 105 has been described. Instead of this, even in a case in which the sample dispensation mechanism 106 or the reactor vessel transfer mechanism 113 accesses the reactor vessel 105, the same advantageous effects can be obtained. In the above-described example, the constitution in which the second light shielding mechanism 118 including the opening part is disposed below the first light shielding mechanism 117 has been described. However, the first light shielding mechanism 117 can also be provided below the second light shielding mechanism 118. Even in this case, although a light shielding range decreases, as will be described, the same advantageous effect can be obtained.

Here, a relation between the disposition of the first and second light shielding mechanisms and a light shielding range will be described with reference to FIG. 13. FIG. 13(a) illustrates a constitution in which the second light shielding mechanism 118 including the opening part is disposed below the first light shielding mechanism 117 and the disposition of the light shielding mechanisms is the same as the disposition illustrated in FIG. 2. FIG. 13(b) illustrates a constitution in which the first light shielding mechanism 117 is disposed below the second light shielding mechanism 118 including the opening part. At this time, the first light shielding mechanism 117 is assumed to be in an open state. Here, r is a radius of the opening part, h is a distance from a light reception position to a lower shutter, and Δh is a distance from the lower shutter to an upper shutter. In a case in which a stray light source is a cause of stray light is at distance of H from the light reception position, a radiation range Ra of the stray light source is (H×r)/(H−h) in FIG. 13(a). In FIG. 13(b), a radiation range Rb of the stray light source is (H×r)/(H−(h+Δh)). Thus, Ra<Rb is satisfied. That is, the range in which light is shield in the constitution in FIG. 13(a) increases.

When a distance between the ports is greater than R, it is possible to prevent light from the stray light source from entering.

<Operation of Light Shielding Mechanism>

Next, an example of an operation of each mechanism of the automated analyzer according to the embodiment, that is, the light shielding mechanism, will be described in more detail.

First, a sample dispensation operation will be described with reference to FIG. 1. In the sample dispensation operation for the reactor vessels 105, the reactor vessel transfer mechanism 113 in the automated analyzer 100 grasps the reactor vessel 105 disposed in the reactor vessel supply unit 110 and transport the reactor vessel 105 to provide the reactor vessel 105 in the sample dispensation port 108. The sample dispensation mechanism 106 is moved onto the sample vessel 101 provided in the sample disk 102 to suck the sample accommodated in the sample vessel 101. After the sample is sucked, the sample dispensation mechanism 106 is moved onto the reactor vessel 105 provided in the sample dispensation port 108 to perform dispensation by ejecting the sample. Subsequently, the reactor vessel transfer mechanism 113 grasps the reactor vessel 105 after the sample dispensation and provides the reactor vessel 105 in the analysis unit 109.

Nest, an operation of the first light shielding mechanism 117 and the second light shielding mechanism 118 at the time of sample dispensation in the analysis unit 109 will be described with reference to FIGS. 5A to 5F. FIGS. 5A to 5E are top views illustrating an operation of the light shielding mechanisms at the time of sample dispensation in the analysis unit according to the embodiment. FIG. 5F is a flowchart illustrating the operation of the light shielding mechanisms at the time of sample dispensation in the analysis unit according to the embodiment. Here, in the embodiment, the time of sample dispensation has been described. The present invention can also be applied to a case of access of another mechanism accesses the reactor vessel, such as the time of providing the reactor vessel 105 in the analysis port 109a or the time of recovery for disposal. In a case in which the light shielding mechanisms according to the embodiment are used at the time of sample dispensation, it is possible to also reduce the influence on the measurement result caused due to scattering by the dispensation in addition to the light shielding from the outside, as described above. As described above, the operations of the first light shielding mechanism 117, the second light shielding mechanism 118, and the reagent dispensation mechanism 107 are controlled by the control unit 114.

FIG. 5A illustrates a state in which the first light shielding mechanism 117 is closed and the second light shielding mechanism 118 is moved so that the opening part 1181 of the second light shielding mechanism 118 is located at No. 1 of the analysis port 109a. Here, as an operation, the first light shielding mechanism 117 first moves in the state in which all the analysis ports are closed (step 501). The second light shielding mechanism 118 is moved so that the opening part 1181 is located at No. 1 which is the position of the predetermined analysis port 109a which is an access target of another mechanism such as the reagent dispensation mechanism 107 (step 502).

Subsequently, when the first light shielding mechanism 117 is moved in the direction 117a in the drawing (step 503), only the second light shielding mechanism 118 is located onto the analysis unit 109 in this state as in FIG. 5B. Here, in the state of FIG. 5B, only No. 1 of the analysis port 109a is exposed through the opening part 1181, and the other analysis ports 109a are shielded from light in this state. Accordingly, even while the photometry is in progress for analysis in the analysis ports 109a other than No. 1 of the analysis port 109a, the access can be made without incidence of disturbance light on the photodetector unit (detector) 116, such as reflected light when the light from the light source 115 at No. 1 of the analysis port 109a hits another mechanism such as the reagent dispensation mechanism 107 or the like, and an operation of ejecting the reagent to the reactor vessel 105 from the opening part 1181 can be performed.

After various operations (step 504) such as the access to No. 1 of the analysis port 109a and the reagent dispensation end, the first light shielding mechanism 117 is moved in the direction 117b in the drawing so that the first light shielding mechanism 117 shields all the analysis ports 109a of the analysis unit 109 from light (step 505) and enters the state of FIG. 5C.

Subsequently, whether there is the analysis port 109a which is a subsequent access target of the mechanism is determined (step 506). Here, for example, in a case in which the reagent is disposed to the reactor vessel 105 at the position of No. 2 of the analysis port 109a, the second light shielding mechanism 118 is moved in the direction 118b in the drawing from the state of FIG. 5C and the opening part 1181 of the second light shielding mechanism 118 is located at the position of No. 2 of the analysis port 109a, as illustrated in FIG. 5D. Here, in the embodiment, the case in which the mechanism first accesses the position of No. 1 of the analysis port 109a and subsequently another mechanism is moved to the position of No. 2 of the analysis port 109a which is a subsequent access target of the mechanism, that is, the case in which the second light shielding mechanism 118 is moved in the direction 118b in the drawing, has been described. However, the second light shielding mechanism 118 is sometimes moved in the direction 118a in the drawing according to a positional relation between the position of the analysis port 109a first accessed by the mechanism and the position of the analysis port 109a which is a subsequent access target.

Thereafter, the first light shielding mechanism 117 is moved in the direction 117a in the drawing and enters the state of FIG. 5E. In the state of FIG. 5E, the access to the reactor vessel 105 provided at the position of No. 2 of the analysis port 109a through the opening part 1181 of the second light shielding mechanism 118 is made to perform the operation such as the reagent dispensation. At this time, because of the second light shielding mechanism 118, disturbance light such as light reflected from the mechanism such as the reagent dispensation mechanism 107 may not enter the analysis port 109a other than the position of the No. 2 of the analysis port 109a. Therefore, it is possible to prevent the light from being incident on the photodetector unit 116 of the analysis port 109a during the photometry.

Conversely, in a case in which the analysis port 109*a* which is the subsequent access target of the mechanism is absent, the operation ends here after FIG. 5C.

In the above-described example, the case of the sequential access from the position of No. 1 of the analysis port 109*a* has been described, but the present invention is not limited thereto. That is, according to the above-described sequence, by performing control such that the opening part 1181 of the second light shielding mechanism 118 is moved to the position of the analysis port 109*a* which is the access target of the various mechanisms, application to various aspects can be without depending on the sequence of the analysis ports 109*a* to be used and the same advantages can be obtained.

Here, FIG. 14 is a time chart illustrating an operation at the time of an analysis operation in the analysis unit according to the embodiment.

As described above, in the state in which all the analysis ports 109*a* are shielded from light by the first light shielding mechanism 117 in the constitution in which the first light shielding mechanism 117 capable of shielding all the analysis ports 109*a* from light and the second light shielding mechanism 118 that includes the opening part and shields some of the analysis ports 109*a* from light among the plurality of analysis ports 109*a* are included in the analysis unit 109 including the plurality of analysis ports 109*a*, the second light shielding mechanism 118 is moved so that the opening part 1181 is located at the position of the predetermined analysis port 109*a*, the second light shielding mechanism 118 is subsequently moved, and the first light shielding mechanism 117 is moved so that the light shielding by the first light shielding mechanism 117 is excluded, and thus the incidence of the disturbance light on the analysis port 109*a* during the analysis is suppressed and the various mechanisms can be accessed to any analysis port 109*a*.

SECOND EMBODIMENT

In the first embodiment, the constitution in which the second light shielding mechanism 118 includes one opening part 1181 has been described. Here, in the embodiment, a constitution in which the second light shielding mechanism 118 includes two opening parts 1181 will be described with reference to FIG. 12.

FIG. 12 is a top view illustrating an operation of light shielding mechanisms at the time of sample dispensation in an analysis unit according to the embodiment. Here, the second light shielding mechanism 118 includes two spaced opening parts 1181 and 1182.

FIG. 12(*a*) illustrates a state in which the first light shielding mechanism 117 is closed after the second light shielding mechanism 118 is moved so that the opening part 1181 of the second light shielding mechanism 118 is located at No. 1 of the analysis port 109*a*. Here, any analysis port 109*a* is not yet located below the opening part 1182 of the second light shielding mechanism 118.

Subsequently, when the first light shielding mechanism is moved in the direction 117*a* in the drawing, only the second light shielding mechanism 118 is located onto the analysis unit 109 in this state as in FIG. 12(*b*). Here, in this state, only No. 1 of the analysis port 109*a* is exposed through the opening part 1181 and all the other analysis ports are shielded from light. Accordingly, even while the photometry is in progress for analysis in the analysis ports 109*a* other than No. 1 of the analysis port 109*a*, the access can be made without incidence of disturbance light on the photodetector unit (detector) 116, such as reflected light when the light from the light source 115 at No. 1 of the analysis port 109*a* hits another mechanism such as the reagent dispensation mechanism 107 or the like, and an operation of ejecting the reagent to the reactor vessel 105 from the opening part 1181 can be performed.

Subsequently, when the first light shielding mechanism 117 is moved in the direction 117*b* in the drawing to shield all the analysis ports 109*a* of the analysis unit 109 from light, the first light shielding mechanism 117 enters the state of FIG. 12(*c*).

Subsequently, in a case in which there is the analysis port 109*a* which is a subsequent access target of the mechanism and the reagent is dispensed to the reactor vessel, for example, at the position of No. 4 of the analysis port 109*a*, the second light shielding mechanism 118 is moved in the direction 118*a* in the drawing from the state of FIG. 12(*c*) and the opening part 1182 of the second light shielding mechanism 118 is located at the position of No. 4 of the analysis port 109*a*, as illustrated in FIG. 12(*d*).

In this way, in the constitution in which the second light shielding mechanism 118 including the two opening parts 1181 and 1182, a movement amount of the second light shielding mechanism 118 may be small in a case of the access to the position of No. 4 after No. 1 of the analysis port 109*a* as in the above-described example. That is, in the case of the second light shielding mechanism 118 including one opening part 1181 according to the first embodiment, the opening part 1181 is moved by three positions of No. 2, No. 3, and No. 4 of the analysis ports 109 in the direction 118*b* in the drawing in order to move the opening part 1181 from the position of No. 1 of the analysis port 109*a* to the position of No. 4. In the second light shielding mechanism 118 according to the embodiment, the opening part 1182 can be located at the position of No. 4 of the analysis port 109*a* by moving the opening part 1182 in the direction 118*b* in the drawing by one position, as described above.

THIRD EMBODIMENT

In the above-described first embodiment, the constitution in which the light source 115 of the analysis unit 109*a* is disposed below the reactor vessel 105 provided in the analysis port 109*a* and the photodetector units (detectors) 116 are disposed on the side surfaces of the reactor vessel 105 provided in the analysis port 109*a* has been described. In the embodiment, a case in which the light source 115 is disposed on a side surface of the reactor vessel 105 provided in the analysis port 109*a* and the photodetector unit (detector) 116 is disposed below the reactor vessel 105 provided in the analysis port 109*a* will be described.

FIG. 6 is a sectional view illustrating the constitution of the analysis port according to an embodiment. As illustrated in the drawing, light from the light source 115 disposed on a side surface of the reactor vessel 105 provided in the analysis port 109*a* is detected by the photodetector unit (detector) 116 disposed below the reactor vessel 105 provided in the analysis port 109*a*.

By disposing the light source 115 on the side surface of the reactor vessel 105 provided in the analysis port 109*a*, it is possible to reduce disturbance light from the light source 115 since only light scattered in the reaction liquid 704 is reflected to the mechanism.

In the above-described example, the number of light sources and the number of photodetector units (detectors) 116 are each set to 1, as described above, but the present invention is not limited thereto, but can be applied to various constitutions. For example, the number of photodetector units 116 can be set to 2 or more or the number of light sources 115 can be set to 2 or more for one reactor vessel 105, or the number of light sources 115 can be set to 1 for the plurality of reactor vessels 105.

FOURTH EMBODIMENT

In the above-described first embodiment, the constitution in which the light source 115 of the analysis port 109a is disposed below the reactor vessel 105 provided in the analysis port 109a and the photodetector units (detectors) 116 are disposed on the side surfaces of the reactor vessel 105 provided in the analysis port 109a has been described. The light source 115 and the photodetector unit (detector) 116 can be disposed together on sides of the reactor vessel 105 provided in the analysis port 109a.

By disposing the light source 115 on the side surface of the reactor vessel 105 provided in the analysis port 109a, it is possible to reduce disturbance light since only light scattered in the reaction liquid 704 in the light from the light source 115 is reflected to the mechanism. In addition, by disposing the photodetector unit (detector) 116 on a side surface of the reactor vessel 105 provided in the analysis port 109a, it is possible to reduce the influence of disturbance light since only light scattered in the reaction liquid 704 in the disturbance light enters the photodetector unit (detector) 116.

As described above, the number of light sources 115 and the number of photodetector units (detectors) 116 are each set to 1, but the present invention is not limited thereto, but can be applied to various constitutions. For example, the number of photodetector units (detectors) 116 can be set to 2 or more or the number of light sources 115 can be set to 2 or more for one reactor vessel 105, or the number of light sources 115 can be set to 1 for the plurality of reactor vessels 105.

FIG. 7 is a top view illustrating the constitution of the analysis port according to the embodiment. As illustrated in the drawing, light from the light source 115 disposed on a side surface of the reactor vessel 105 provided in the analysis port 109a can be detected by the photodetector unit (detector) 116 disposed on another side surface of the reactor vessel 105 provided in the analysis port 109a.

FIFTH EMBODIMENT

In the first embodiment, the device that performs blood coagulation analysis as an example of the automated analyzer has been described using the constitution of a standalone type of device operated particularly as one independent device.

Incidentally, as an automated analyzer for clinical examination, in addition to the standalone type of device, there is a module type constitution in which analysis units of a plurality of analysis fields such as biochemical analysis, immune analysis, and blood coagulation analysis are connected to be operated as one device as a whole using a common sample rack transport line for operational efficiency of an examination laboratory.

In the embodiment, an application example of an automated analyzer including blood coagulation analysis units of two modules will be described with reference to FIG. 9 as an example of a module type of automated analyzer.

Here, although not illustrated in the drawing, the first light shielding mechanism 117 and the second light shielding mechanism 118 according to the embodiment are applied to analysis units 926 and 927 in FIG. 9 and an analysis unit 1006 in FIG. 10, respectively. Since the constitution of the light shielding mechanisms is the same as that of the above-described embodiments, the detailed description thereof will be omitted. Here, in the case of the module type of device, the number of analysis ports in each analysis unit is greater than that of the standalone type of device.

FIG. 9 is a diagram illustrating a basic constitution of an automated analyzer including blood coagulation analysis units of two modules according to the embodiment. As illustrated in the drawing, a module type of automated analyzer 900 includes a first blood coagulation analysis unit 912 and a second blood coagulation analysis unit 917 which are a plurality of analysis units analyzing a reaction liquid which is a liquid mixture consisting of a sample and a reagent and includes transport lines 904 and 905 which transport a sample rack 901 on which sample vessels accommodating samples are mounted in order to supply the sample to each analysis unit.

As an example of a transport system that transports the sample rack 901 on which the sample vessel in which a sample such as blood plasma which is an analysis target is entered is mounted, the drawing illustrates a rack supply unit 902 which supplies the sample rack 901 onto the transport line 904; a rack reception unit 903 which accommodates the sample rack 901 transmitted onto the transport line 905 after the analysis ends; a transport line (in an advance direction) 904 and a transport line (in a return direction) 905 which transport the sample rack 901 to each analysis unit, a rack standby unit 906 which allows the sample rack waiting for analysis to stand by; a rack handling mechanism 907 which transfers the sample rack 901 between the transport lines 904 and 905 and the rack standby unit 906 and in the rack standby unit 906; a rack dispensation mechanism 909 which dispenses a destination of the rack on the transport line 905 based on information regarding the sample rack 901; a rack returning mechanism 908 which moves the distributed sample rack 901 to the rack reception unit 903; an emergency sample rack inserting unit 910 which inserts the sample rack 901 in which emergency analysis is necessary; and a reading unit (transport line) 911 which reads information such as a barcode attached to the sample rack 901 on the transport line 904.

A transport system of the first blood coagulation analysis unit 912 disposed along the transport line 904 includes: a reading unit (first blood coagulation analysis unit) 916 which compares analysis request information regarding the sample accommodated in the sample rack 901 from the transport line 904; a first rack carrying mechanism 914 which receives the sample rack 901 from the transport line 904; a first dispensation line 913 which includes a sampling area to which the sample is dispensed and in which the sample rack 901 can stand by until start of the dispensation of the sample; and a first rack handling mechanism 915 which reversely transports the sample rack 901 to the transport lines 904 and 905 after the dispensation of the sample.

As in the constitution of the transport system of the second blood coagulation analysis unit 912 described above, a transport system of the second blood coagulation analysis unit 917 disposed along the transport line 904 includes: a reading unit (first blood coagulation analysis unit) 921 which compares analysis request information regarding the sample accommodated in the sample rack 901 from the transport line 904, a second rack carrying mechanism 919 which receives the sample rack 901 from the transport line 904, a second dispensation line 918 which includes a sampling area to which the sample is dispensed and in which the sample rack 901 can stand by, and a second rack handling mechanism 920 which reversely transports the sample rack 901 to the transport lines 904 and 905 after the dispensation of the sample.

As a whole, the control unit 922 controls condition settings or operations of various constitutions of the automated analyzer 900 such as a transport operation for the above-described sample rack 901, an operation of dispensation a sample or a reagent, an operation of distributing and carrying in and out a sample 901 based on reading information, a data processing operation such as a blood coagulation time or calculation of the density of a target component based on a detection result. An input unit 925 such as a keyboard which inputs various kinds of data regarding analysis conditions, an instruction, or the like from an operator, a storage unit 923 which stores the input information, reading information from the sample, the reagent, and the like, and information regarding the detection result, and an output unit 924 which displays a graphical user interface (GUI) related to the detection result and various operations of the automated analyzer 900 are connected to the control unit 922. In the drawing, the control unit 922 can be connected to each constituent unit to control the whole automated analyzer and can also be configured to include a control unit independent for each constituent unit.

Next, the constitution of the blood coagulation analysis unit described above with reference to FIG. 10 will be described in more detail. In FIG. 10, the blood coagulation analysis unit includes: a sample dispensation mechanism 1017 which dispenses the sample accommodated in the sample vessel on the sample rack to a reactor vessel 1001 used for measurement; a sample dispensation port 1016 in which the reactor vessel 1001 which is a target of the sample dispensation operation can be disposed; a standby unit 1011 which includes a plurality of standby ports 1010 accommodating the reactor vessel in a standby state; a reactor vessel transfer mechanism 1012 which transports the reactor vessel 1001 and a reactor vessel magazine 1002 in which the plurality of reactor vessels 1001 are stocked and carries in and out to each position as necessary; a preheating port 1009 which includes a plurality of preheating ports 1008 of which temperature is adjusted to 37° C. to increase the temperature of a sample immediately before measurement of a blood coagulation time or a preprocessed sample subjected to a process such as dilution; an analysis unit 1007 which includes a plurality of analysis ports 1010 of which temperature is similarly adjusted to 37° C. to measure a blood coagulation time; a reagent disk 1004 in which reagent cassettes 1003 containing a reagent bottle in which a reagent is enclosed are disposed in a circumferential form and of which temperature is adjusted to about 10° C.; a reagent cassette transport mechanism 1015 which transports the reagent cassettes 1003 disposed in the reagent cassette supply unit 1013 to the reagent disk 1004; a reagent information reading unit 1005 which reads a barcode in which a measurement item of the reagent cassette 1003 transported to the reagent disk 1004, an expiration date, or the like is input or reagent information from a medium such as RFID; a reagent cassette reception unit 1014 which receives the reagent cassette 1003 no longer used and taken out from the reagent disk 1004 by the reagent cassette transport mechanism 1015; a reactor vessel discarding unit 1023 which discards the used reactor vessel 1001; a sample probe cleaning tank 1018 which cleans a sample probe; a first reagent probe cleaning tank 1020 which cleans a reagent probe of the first reagent dispensation mechanism 1019; and a second reagent probe cleaning tank 1022 which cleans a reagent probe of the second reagent dispensation mechanism 1021.

Here, although not illustrated in the drawing, as in the above-described embodiments, each of the analysis ports 1010 in the analysis unit 1007 includes an optical system including a light source which radiates light to a reaction liquid which is a liquid mixture consisting of a sample and a reagent accommodated in the reactor vessel 1001 and a photodetector unit (detector) which detects light from the light source.

A blood coagulation time is measured through calculation in the control unit 922 based on data of the detected light.

SIXTH EMBODIMENT

In the fifth embodiment, the automated analyzer including the blood coagulation analysis unit of two modules has been described. Here, an application example to a module type automated analyzer including a plurality of analysis unit for different analysis fields will be described with reference to FIG. 11.

Here, although not illustrated in the drawing, the constitutions of the first light shielding mechanism 117 and the second light shielding mechanism 118 and the analysis units 926 and 927 in FIG. 11 according to the embodiment are the same as those of the above-described embodiment. Therefore, the detailed description thereof will be omitted. However, in the case of the module type device, the number of analysis ports in each analysis unit is greater than that of the standalone type of device. Each of the analysis ports in the analysis units 926 and 927 includes an optical system including a light source that radiates light to a reaction liquid which is a liquid mixture consisting of a reagent and a sample accommodated in the reactor vessel and a photodetector unit (detector) that detects the light from the light source, as in the above-described embodiments.

FIG. 11 is a diagram illustrating a basic constitution of the automated analyzer including a biochemical analysis unit and a blood coagulation analysis unit according to the embodiment. An automated analysis device 1100 is different from the automated analyzer 900 according to the fourth embodiment in that a biochemical analysis unit 1101 is included in addition to the first blood coagulation analysis unit 912 and the second blood coagulation analysis unit 917 described above. Although not illustrated in detail in the drawing, the biochemical analysis unit 1101 includes a reagent disk 1102 on which a sample dispensation mechanism sucking a sample from a sample rack 1104 and ejecting the sample into the reactor vessel and the reagent vessel accommodating a reagent are mounted and a reaction disk 1103 which includes a reagent dispensation mechanism sucking the reagent from the reagent vessel and ejecting the reagent into the reactor vessel and an optical system including a light source that radiates light to a reaction liquid and a photodetector unit (detector) that detects the light from the light source. The control unit 922 obtains the density of an object component or the like based on data detected in the biochemical analysis unit 1101 by calculation.

The disposition of the biochemical analysis unit 1101, the first blood coagulation analysis unit 912, and the second blood coagulation analysis unit 917 is not particularly limited. To suppress congestion of the sample rack 1004, it is preferable to dispose the biochemical analysis unit 1101 having a high specimen processing ability on the upstream side, that is, near a position at which the sample rack is supplied.

The present invention is not limited to the foregoing embodiments and includes various modification examples. For example, the foregoing embodiments have been described in detail in order to facilitate the understanding of the present invention, and the present invention is not limited to a case in which the described constitutions are necessarily provided. Some of the constitutions of a certain embodiment can be substituted with the constitutions of another embodiment and the constitutions of another embodiment can also be added to the constitutions of a certain embodiment. Addition, deletion, or substitution of other constitutions can be made in some of the constitutions of each embodiment.

REFERENCE SIGNS LIST 100 automated analyzer
101 sample vessel
102 sample disk
103 reagent vessel
104 reagent disk
105 reactor vessel
106 sample dispensation mechanism
107 reagent dispensation mechanism
107a reagent dispensation probe
108 sample dispensation port
109 analysis unit
109a analysis port
110 reactor vessel supply unit
111 cleaning mechanism
112 reactor vessel discarding unit
113 reactor vessel transfer mechanism
114 control unit
115 light source
116 photodetector unit (detector)
117 first light shielding mechanism
117a, 117b movement direction of first light shielding mechanism
118 second light shielding mechanism
118a, 118b movement direction of second light shielding mechanism
1181, 1182 opening part of second light shielding mechanism
704 reaction liquid (liquid mixture consisting of sample and reagent)
900 automated analyzer (module type)
901 sample rack
902 rack supply unit
903 rack reception unit
904 transport line (in advance direction)
905 transport line (in return direction)
906 rack standby unit
907 rack handling mechanism
908 rack returning mechanism
909 rack distribution mechanism
910 emergency sample rack inserting unit
911 reading unit (transport line)
912 first blood coagulation analysis unit
913 first dispensation line
914 first rack carrying mechanism
915 first rack handling mechanism
916 reading unit (first blood coagulation analysis unit)
917 second blood coagulation analysis unit
918 second dispensation line
919 second rack carrying mechanism
920 second rack handling mechanism
921 reading unit (second blood coagulation analysis unit)
922 control unit
923 storage unit
924 output unit
925 input unit
926 first analysis unit
927 second analysis unit
1001 reactor vessel
1002 reactor vessel magazine
1003 reagent cassette
1004 reagent disk
1005 reagent information reading unit
1006 analysis port
1007 analysis unit
1008 preheating port
1009 preheating unit
1010 standby port
1011 standby unit
1012 reactor vessel transfer mechanism
1013 reagent cassette supply unit
1014 reagent cassette reception unit
1015 reagent cassette transport mechanism
1016 sample dispensation port
1017 sample dispensation mechanism
1018 sample probe cleaning tank
1019 first reagent dispensation mechanism
1020 first reagent probe dispensation mechanism
1021 second reagent dispensation mechanism
1022 second reagent probe cleaning tank
1023 reactor vessel discarding unit
1100 automated analyzer (module type)
1101 biochemical analysis unit
1102 reagent disk
1103 reaction disk
1104 sample disk

The invention claimed is:
1. An automated analyzer comprising:
a reactor vessel configured to accommodate a liquid mixture consisting of a sample and a reagent;
a sample dispensation mechanism configured to dispense the sample to the reactor vessel;
a reagent dispensation mechanism configured to dispense the reagent to the reactor vessel;
an analysis unit that includes a plurality of analysis ports, each including an optical system formed by a light source radiating light to the reactor vessel accommodating the liquid mixture, a groove in which the reactor vessel is accommodated, and a photodetector unit receiving the light radiated from the light source;
a first movable light shielding mechanism configured to be movable by a first driving unit in a first direction of the analysis unit and, when positioned directly above the analysis unit, shields all the analysis ports from light entering from above the analysis unit among the plurality of analysis ports;
a second movable light shielding mechanism that includes an opening part that allows light to pass through the second movable light shielding mechanism, is configured to be movable by a second driving unit in a second direction of the analysis unit that is perpendicular to the first direction, and, when positioned directly above the analysis unit, shields some of the analysis ports from light reflected from the reagent dispensation mechanism among the plurality of analysis ports; and
a control unit configured to control operations of the sample dispensation mechanism, the reagent dispensa- tion mechanism, the first movable light shielding mechanism, and the second movable light shielding mechanism, wherein, in a state in which all the analysis ports are shielded from external light from outside of the analysis unit by the first movable light shielding mechanism, the control unit controls movement of the second movable light shielding mechanism with the second driving unit to place the opening part at a position of a predetermined analysis port, and wherein, in a state in which the opening part of the second movable light shielding mechanism is placed at the position of the predetermined analysis port, the first movable light shielding mechanism is subsequently moved so that the first movable light shielding mechanism does not shield the analysis ports and light is allowed to pass through the opening part.

2. The automated analyzer according to claim 1, wherein the control unit controls the sample dispensation mechanism and the reagent dispensation mechanism to access the predetermined analysis port through the opening part.

3. The automated analyzer according to claim 2, wherein the control unit controls the optical system such that the light is radiated by the light source to the reactor vessel accommodated in the analysis port and the external light is received through the opening part when the sample dispensation mechanism and the reagent dispensation mechanism access the predetermined analysis port.

4. The automated analyzer according to claim 1, further comprising:
a transfer mechanism configured to transport the reactor vessel into and out of a predetermined position of the analysis port,
wherein the control unit controls the transfer mechanism such that the transfer mechanism accesses the predetermined analysis port through the opening part.

5. The automated analyzer according to claim 4, wherein the control unit controls the optical system such that the light is radiated by the light source to the reactor vessel accommodated in the analysis port and the external light is received when the transfer mechanism accesses the predetermined analysis port through the opening part.

6. The automated analyzer according to claim 1, further comprising:
a transfer mechanism configured to transport the reactor into and out of a predetermined position of the analysis port,
wherein the control unit performs control such that at least one of the sample dispensation mechanism, the reagent dispensation mechanism, and the transfer mechanism accesses the predetermined analysis port through the opening part.

7. The automated analyzer according to claim 1, wherein the light source is arranged below a bottom end of the reactor vessel held in the analysis port.

8. The automated analyzer according to claim 1, wherein the photodetector unit is arranged below a bottom end of the reactor vessel held in the analysis port.

9. The automated analyzer according to claim 1, wherein the analysis unit is configured such that the plurality of analysis ports are disposed in series.

10. An automated analyzer comprising:
a transport line configured to transport a sample rack holding a sample vessel which accommodates a sample;
a plurality of analysis units that are disposed along the transport line; and
a control unit configured to control transportation of the sample rack,
wherein each of the analysis units includes
a sample dispensation mechanism configured to dispense the sample accommodated in the sample vessel held in the sample rack on the transport line to a reactor vessel in the analysis unit,
a reagent dispensation mechanism configured to dispense a reagent to the reactor vessel to which the sample is dispensed,
a plurality of analysis ports, each including an optical system formed by a light source radiating light to the reactor vessel accommodating the liquid mixture consisting of the sample and the reagent, a groove in which the reactor vessel is accommodated, and a photodetector unit receiving the light radiated from the light source,
a first movable light shielding mechanism configured to be movable by a first driving unit in a first direction of the analysis unit and, when positioned directly above the analysis unit, shields all the analysis ports from light entering from above the analysis unit among the plurality of analysis ports,
a second movable light shielding mechanism that includes an opening part that allows light to pass through the second movable light shielding mechanism, is movable by a second driving unit in a second direction of the analysis unit that is perpendicular to the first direction, and, when positioned directly above the analysis unit, shields some of the analysis ports from light reflected from the reagent dispensation mechanism among the plurality of analysis ports, and
a control unit configured to control operations of the sample dispensation mechanism, the reagent dispensation mechanism, the first movable light shielding mechanism, and the second movable light shielding mechanism,
wherein, in a state in which all the analysis ports are shielded from external light from outside of the analysis unit by the first movable light shielding mechanism, the control unit controls movement of the second movable light shielding mechanism with the second driving unit to place the opening part at a position of a predetermined analysis port, and
wherein, in a state in which the opening part of the second movable light shielding mechanism is placed at the position of the predetermined analysis port, the first movable light shielding mechanism is subsequently moved so that the first movable light shielding mechanism does not shield the analysis ports and light is allowed to pass through the opening part.

11. An analysis method in an automated analyzer including
a reactor vessel that accommodates a liquid mixture consisting of a sample and a reagent,
a sample dispensation mechanism configured to dispense the sample to the reactor vessel,
a reagent dispensation mechanism configured to dispense the reagent to the reactor vessel,
an analysis unit that includes a plurality of analysis ports, each including an optical system formed by a light source radiating light to the reactor vessel accommodating the liquid mixture, a groove in which the reactor vessel is accommodated, and a photodetector unit receiving the light radiated from the light source, a first movable light shielding mechanism configured to be movable by a first driving unit in a first direction of the analysis unit and, when positioned directly above the analysis unit, shields all the analysis ports from light entering from above the analysis unit among the plurality of analysis ports, a second movable light shielding mechanism that includes an opening part that allows light to pass through the second movable light shielding mechanism, is movable by a second driving unit in a second direction of the analysis unit that is perpendicular to the first direction, and, when positioned directly above the analysis unit, shields some of the analysis ports from light reflected from the reagent dispensation mechanism among the plurality of analysis ports, and a control unit configured to control operations of the sample dispensation mechanism, the reagent dispensation mechanism, the first movable light shielding mechanism, and the second movable light shielding mechanism, the method comprising:

controlling, by the control unit, movement of the second movable light shielding mechanism using the second driving unit to place the opening part at a position of a predetermined analysis port in a state in which all the analysis ports are shielded from external light from outside of the analysis unit by the first movable light shielding mechanism, and subsequent to the opening part of the second movable light shielding mechanism being placed at the position of the predetermined analysis port, controlling, by the control unit, movement of the first movable light shielding mechanism using the first driving unit so that the first movable light shielding mechanism does not shield the analysis ports and light is allowed to pass through the opening part.

* * * * *